United States Patent [19]

Kricka et al.

[11] Patent Number: 5,110,745
[45] Date of Patent: May 5, 1992

[54] METHODS OF DETECTING GLYCATED PROTEINS

[75] Inventors: Larry J. Kricka, Berwyn; Peter Wilding, Paoli, both of Pa.

[73] Assignee: The Trustees of the University of Pennsylvania, Philadelphia, Pa.

[21] Appl. No.: 359,953

[22] Filed: Jun. 1, 1989

[51] Int. Cl.⁵ .............................................. G01N 33/52
[52] U.S. Cl. ........................................ 436/87; 436/67; 436/178; 436/501; 436/518; 436/815
[58] Field of Search ................ 436/67, 87, 88, 164, 436/175, 178, 501, 518, 815

[56] References Cited

U.S. PATENT DOCUMENTS

| | | | |
|---|---|---|---|
| 4,200,435 | 4/1980 | Stroupe | 23/230 |
| 4,247,533 | 1/1981 | Cerami et al. | 424/1 |
| 4,255,385 | 3/1981 | Stroupe | 422/61 |
| 4,269,605 | 5/1981 | Dean et al. | 23/230 |
| 4,349,352 | 9/1982 | Manning | 23/230 |
| 4,399,227 | 8/1983 | Niederau | 436/67 |
| 4,629,692 | 12/1986 | Dean | 436/67 X |
| 4,642,295 | 2/1987 | Baker | 436/87 |
| 4,645,742 | 2/1987 | Baker . | |
| 4,820,636 | 4/1989 | Hill et al. | 436/67 X |
| 4,861,728 | 8/1989 | Wagner | 436/67 X |
| 4,876,188 | 10/1989 | Smith et al. | 436/67 X |

FOREIGN PATENT DOCUMENTS 0227171 10/1985 Japan ................................. 436/67
82/01804 5/1982 World Int. Prop. O. ............ 436/67

OTHER PUBLICATIONS

Scouten et al., Solid Phase Biochemistry, Wiley, New York, Chapter 4, pp. 149-187, (1983).

Primary Examiner—Robert J. Hill, Jr.
Attorney, Agent, or Firm—Woodcock Washburn Kurtz Mackiewicz & Norris

[57] ABSTRACT

The invention discloses novel methods of detecting glycated proteins in test samples of blood and methods of detecting chronic hyperglycemia. The test sample is contacted with a binder composition under conditions which allow binding of glycated protein in the test sample to at least a portion of the binder composition. The test sample is then exposed to a glycated compound affixed to a solid support under conditions which allow raction of unbound binder composition from the previous step to at least a portion of the glycated compound on the solid support. The glycated compound affixed to a solid support from the previous step which did not react with the unbound binder composition is then reacted with a detecting agent and the detecting agent is detected.

33 Claims, 16 Drawing Sheets

```
GLYCATED PROTEIN + BINDER
              ⇅
   GLYCATED PROTEIN : BINDER
              ↓
           BINDER
            ∙ ∙                          INDICATOR
                                            (
   GLYCATED COMPOUND     GLYCATED COMPOUND  ⤳  SIGNAL
   ─────────┴─────────────────────┴──────────────────
                    SOLID SUPPORT
```

METHODS OF DETECTING GLYCATED PROTEINS

FIELD OF THE INVENTION

The invention relates to the field of assays for the detection of biological compounds.

BACKGROUND OF THE INVENTION

Blood glucose reacts continuously with proteins in the circulation of human beings. In particular human beings such glucose may bind to amino groups of protein to form aldimines, Schiff bases, which undergo molecular (Amadori) rearrangement to form stable ketosamines.

The various plasma protein-ketosamine products are known as "fructosamines". This reaction occurs predominantly with albumin present in the plasma. Glycation occurs principally (33%) at the lysine residue at position 52 of the albumin. Other sites of glycation include Lys-199, Lys-281, and Lys-439 and there is evidence to support glycation occurring at Lys-12, Lys-233, Lys-317, Lys-351 and Lys-534. Glycation alters the conformation of albumin, as determined by fluorescence studies of the sole tryptophan residue at position 214, and influences the binding properties of albumin. Binding of fatty acids, hemin, bilirubin, and certain drugs is diminished. Reaction also occurs with hemoglobin inside red blood cells to form glycosylated hemoglobin (e.g., hemoglobin Alc). This glycation is believed to occur at the terminal valine residue of the beta chain.

When blood glucose is in proper hormonal balance, glycated protein formation is minimal. However, when blood glucose concentration is elevated for significant periods due to lack of appropriate hormonal control, as in a diabetic patient, then glycated protein concentration, measured as fructosamine concentration in plasma or hemoglobin Alc in blood is elevated above 2 mmol/l and 8%, respectively. Plasma albumin has a metabolic half-life of seventeen days, thus measurement of fructosamine concentration in serum or plasma provides a retrospective record of blood glucose concentrations during the preceding 7–21 days. The metabolic half-life of hemoglobin, packaged inside a red blood cell, is 60–90 days. Thus, testing the amount of glycated hemoglobin provides a retrospective record of control or compliance during the previous 60–90 days. Individually these tests provide different, more relevant, clinical information than a blood glucose measurement which only reflects the current status of glucose metabolism.

A number of tests have been devised to determine the concentration of fructosamines in blood. U.S. Pat. No. 4,200,435 issued Apr. 29, 1980 to Stroupe and U.S. Pat. No. 4,255,385 issued Mar. 10, 1981 to Stroupe disclose methods, test kits and reagents for detecting glycosylated hemoglobin in blood by measuring the change in distribution of the allosteric forms of hemoglobin in blood samples. U.S. Pat. No. 4, 247,533 issued Jan. 27, 1981 to Cerami et al., discloses antibodies specific for glycohemoglobin Alc for use in immunoassays for detecting fructosamines in blood. U.S. Pat. No. 4,269,605 issued May 26, 1981 to Dean et al., discloses methods of separating glycoproteins from non-glycosylated proteins in a mixture by binding the glycoproteins to a dihydroxyboryl group bonded to a support. Generally, this takes the form of passing a blood sample through a column containing the reactive agent where glycoproteins bind to the dihydroboronyl group. Non-binding components blood are washed away, and the glycoproteins are then eluted from the column.

In the method disclosed in U.S. Pat. No. 4,349,352 issued Sep. 14, 1982 to Manning, isolated glycoprotein is treated with a phenylhydrazine and the absorption coefficient of the resulting phenylhydrazine is then measured. U.S. Pat. No. 4,399,227 issued Aug. 16, 1983 to Niederau, discloses a method of reducing interference by unstable glucose-aldimine-hemoglobin compounds with an assay for determining glycosylated hemoglobin. These tests, however, can be time-consuming and labor-intensive to perform. Persons suffering from diabetes must have their blood glucose levels checked regularly to assure the proper efficacy of their treatment. Time-consuming tests that cannot be performed in the physician's office while the patient is present are inconvenient and increase the likelihood of patient non-compliance with the prescribed treatment.

U.S. Pat. No. 4,642,295 issued Feb. 10, 1987 to Baker and U.S. Pat. No. 4,645,742 issued Feb. 24, 1987 to Baker disclose tests and reagents for determining fructosamine levels in blood by reacting a blood sample with a coloring agent, taking a first measurement of light absorption and at a suitable later time, taking a second light absorption measurement, and comparing any change in measurements, such that any change in color between the first and second measurement is caused predominantly by glucose in the sample that is reacted or associated with an amine group of protein and has undergone a molecular rearrangement to form fructosamine. This test is relatively inexpensive and simple to perform, but is subject to a certain amount of interference by other components of blood.

There is thus a need for rapid, reliable tests for detection of fructosamines in blood that can be performed by relatively unskilled personnel without the need for sophisticated laboratory equipment. Accordingly, it is an object of the invention to provide such tests for measuring levels of fructosamines in blood.

SUMMARY OF THE INVENTION

The present invention provides novel methods of detecting glycated proteins in blood for use in diagnosis and for following the treatment of diabetes and other conditions wherein levels of glycated proteins in blood is indicated. In accordance with preferred embodiments, a test sample of blood is contacted with a binder composition under conditions which allow binding of glycated protein in the test sample to at least a portion of the binder composition. The test sample is then exposed to glycated compound affixed to a solid support under conditions which allow reaction of unbound binder composition from the prior step to at least a portion of the glycated compound on the solid support. Next the glycated compound affixed to a solid support from step (b) which has not been reacted with the unbound binder composition is reacted with a detecting agent. The detecting agent is then detected. The presence of detecting agent indicates the presence of glycated protein in the test sample. The methods of the invention may be performed in a quantitative manner wherein the binding of glycated protein in the test sample to binder composition, the reaction of unbound binder composition with glycated composition affixed to the solid support, and the reaction of unbound glycated composition the detecting agent are each substantially quantitative.

This invention also provides methods of detecting chronic hyperglycemia in mammals, preferably humans, whereby the presence of bound detecting agent indicates the presence of glycated components in the test sample and the presence in the mammal of chronic hyperglycemia.

Preferred embodiments of this invention utilize a novel interaction between a boronate binder composition and a glycated compound bound to a solid support which is preferably an exogenous fructosamine, or other compound with a 1,2- cis diol group which modulates the properties of the fructosamine. The glycated compound, an exogenous fructosamine, is then detected rather than the endogenous fructosamine, thus avoiding or minimizing interferences between the detecting agent and other blood components. The glycated compound is detected with a detecting agent such nitro blue tetrazolium (NBT), in a reaction which can be readily detected by visual inspection. The exogenous fructosamine is present in an immobilized form to facilitate separation of unreacted boronate from the sample and boronateglycated protein complexes. This format also permits easy performance of the methods of the invention. The methods of the present invention are suitable inter alia, for assay of total glycated proteins in plasma or whole blood.

The methods of the present invention have several advantages over available tests for measuring the levels of fructosamines in blood. The glycated protein may be colored as this will not interfere in the assay. This is not the case for some of the prior methods. The methods of the invention can detect both glycated hemoglobin and glycated albumin during the same test, thus improving over prior tests which determined the level of only one of these compounds. Interference by substances present in complex biological fluids are minimized by the novel assay format. Interference is minimized by detecting the glycated protein indirectly through a binder composition and glycated compound. Other components of the biological sample are removed by the methods of the invention, leaving minimal amounts of material to cross-react or interfere with binding of the detecting agent to the glycated compound.

DETAILED DESCRIPTION OF THE PREFERRED EMBODIMENTS

Figure 1A:
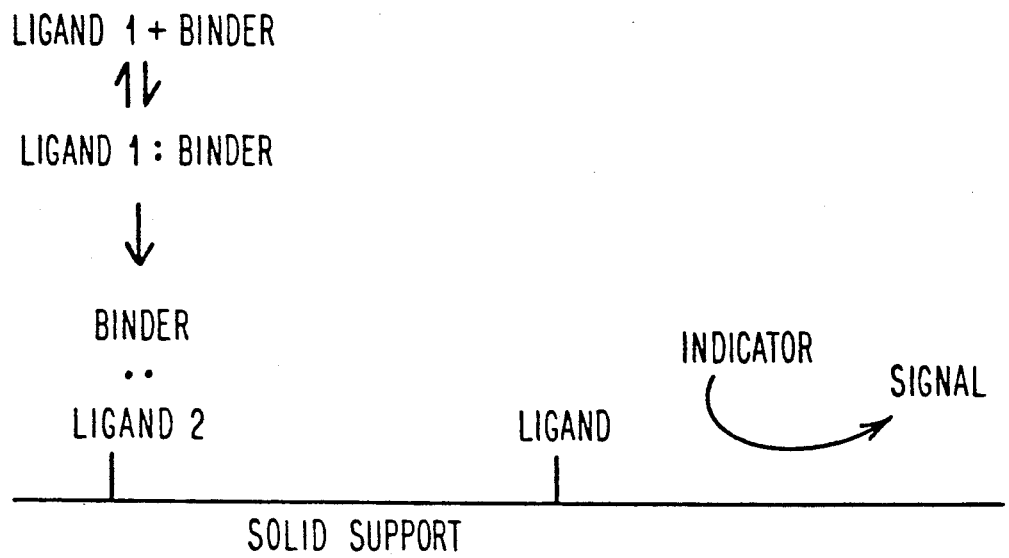
FIG. 1 shows a diagramatic representation of the methods of the invention.

A general diagramatic description of the invention is shown in FIG. 1(A). The test sample suspected of containing ligand 1 and the binder are allowed to bind. Unreacted binder from this step is contacted with ligand 2 which is bound to a solid support, so that unreacted binder from the previous step binds to ligand 2. Indicator (or detecting agent) is then reacted with ligand 2 that did not react with the binder and the signal from the indicator is then detected. The amount of ligand 1 in the test sample can be quantified by contacting a known quantity of the binder with the test sample and then contacting the binder with a known quantity of ligand 2. The greater the amount of ligand 1 in the test sample, the smaller the amount of binder to react with ligand 2 and the greater the amount of ligand 2 to react with the indicator. The opposite result will be obtained when a small amount of ligand 1 is present in the test sample.

Figure 1B:
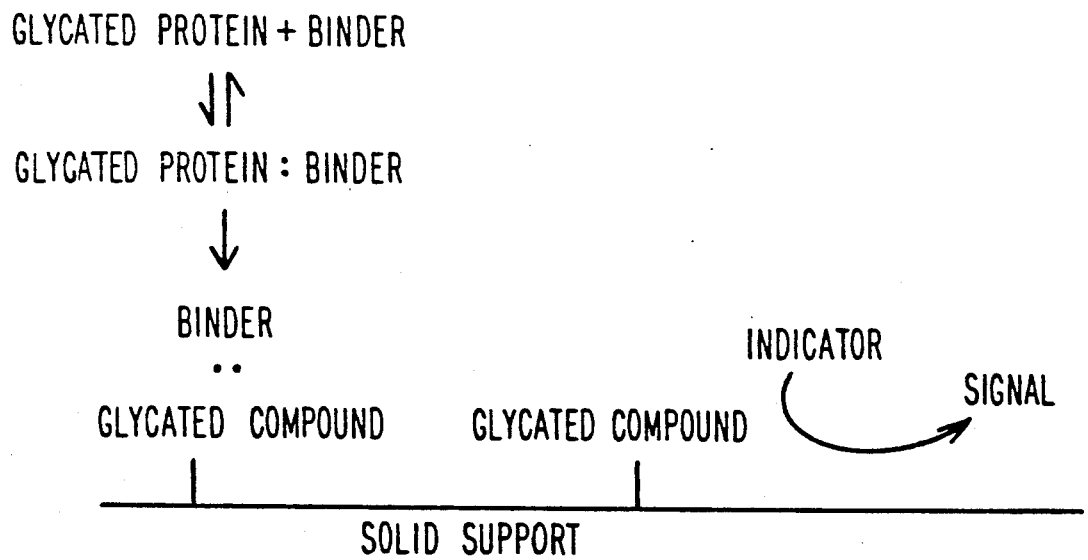

The methods of the invention are preferably performed, as shown in FIG. 1(B), by contacting a test sample of blood or other body fluid suspected of containing glycated protein with the binder composition for a length of time sufficient for at least a portion of the binder composition to bind to glycated protein in the test sample. In some embodiments of the invention, binding is very rapid, so that binding occurs in a few minutes; in others binding may be complete only after an extended period of time. It is preferable that the binder composition be present in excess amounts so there is excess binder composition to bind to the glycated compound. If a test sample is suspected of containing more of the glycated protein than can bind to the binder composition, the test sample can be diluted or divided to bring the amount of the glycated protein within the range of the binder composition.

In the next step, the test sample is contacted with a glycated compound which is affixed to a solid support, for a length of time and under conditions sufficient for the excess binder composition of the previous step to bind to at least a portion of the glycated compound. Again, binding may be very rapid, so that binding is complete within a few minutes, but in other embodiments of the invention binding may not be complete for an extended period of time.

The glycated compound affixed to the solid support is then contacted with a detecting agent for a length of time sufficient for the detecting agent to bind to glycated compound and finally the detecting agent is detected.

In the performance of the methods of the invention, it may be desirable to wash the solid support after exposure to the test sample and unbound binder composition to remove cellular debris and complexes of the glycated protein and binder composition, so that any interference with the binding of glycated compound affixed to the solid support and detecting agent is minimized.

In the methods of the invention, the glycated protein to be detected, glycated compound and the binder composition are chosen to have a sufficient binding affinity for each other such that interference from cellular or exogenous components is minimized. The glycated protein to be detected and the glycated compound may be the same or different compounds. The glycated compound bound to the solid support may be any type of biological compound for which a binder in accordance with this invention occurs naturally or can be constructed. Preferred compounds include but are not limited to glycoproteins, carbohydrates and nucleosides. The glycated compound may also be a synthetic compound such as glycated polylysine.

The binder composition may be any type of naturally occurring or synthetic compound that has a binding affinity for glycated compounds. It is preferable in certain preferred embodiments of the invention that the binder composition have minimal binding capacity for other cellular or exogenous components to which it will be exposed. A preferred binder composition for glycated components of blood is

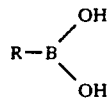

wherein R is hydroxyl, phenyl or optionally substituted phenyl. Suitable substituents for phenyl include alkyl, phenyl and nitro substituents which can be positioned at any selected carbon of the phenyl ring. Examples of suitable binder compositions include boric acid and meta-aminophenyl boronic acid. Although boric acid and derivatives are known to bind to compounds having a cis-1-2 diol configuration such as carbohydrates, glycoproteins, catecholamines and nucleosides, the majority of the components in blood or plasma having this type of configuration are glycated proteins, so that there is little interference from these compounds.

The detecting agent may be any type of compound that is capable of binding with the glycated compound. The detecting agent is preferably a chromogenic agent but fluorescent, phosphorescent, chemiluminescent, bioluminescent, radiographic or other types of agents are also suitable for use in the methods of the invention. In preferred embodiments of the invention, the detecting agent is a chromogenic agent, more preferably a tetrazolium derivative or salt, such as nitro blue tetrazolium 3-(4,5-dimethylthiazol-2-yl)2,5-phenyltetrazolium bromide and 5-phenyltetrazolium bromide. It is also preferable that the detecting agent is unreactive, or has low levels of interaction, with the solid support, to minimize non-specific binding with the solid support that could distort the results obtained with the methods of the invention.

The detecting agent is detected by standard techniques suitable for the particular detecting agent used in the methods of the invention. For example, when chromogenic agents are used, methods such visual inspection and spectrophotometric analysis are suitable. Other suitable methods for use with other detecting agents include radiographic and fluorometric methods.

The solid support for use in the methods of the invention may be any conventional type of solid support used in immunoassays or other types of biological assays that is capable of binding the glycated compound and has minimal interactions with the detecting agent. Suitable solid supports include nitrocellulose, synthetic polymeric matrices and polystyrenes.

When whole blood is used in the methods of the invention, blood cells may be lysed prior to the first step so that glycated hemoglobin can be more readily detected. Lysing of the cells may be done by any convenient method for lysing of cells using commercially available reagents.

The invention also provides kits for performance of the methods of the invention. The kits comprise a solid support and reagents in separate containers comprising glycated compound, binder composition and detecting agent. The glycated compound may be supplied bound to the solid support for convenience in performance of the methods of the invention. The kits may also comprise a standards chart for comparing the results obtained with test samples with results obtained using known quantities of the glycated protein for quantitation of the amount of glycated protein in the test sample.

It is expected that the methods of the invention will be useful for detection of other types of ligands in liquid solution. For example, nucleosides can be detected using the preferred binder compositions, by testing for their presence in whole or fractionated cell preparations. Alternatively, other ligand/binder composition pairs such as enzyme/enzyme inhibitor or activator can be employed as ligand 1, binder and ligand 2. It is only necessary that the ligand and binder composition have sufficient binding affinity for each other that there is little interference from binding with other components present.

EXAMPLES

Preparation of Glycated Hemoglobin (G-Hb)

G-Hb was isolated from blood of a diabetic patient (G-Hb, 20%) using a Glyc-Affin test kit (IsoLab Inc., Akron, Ohio). The isolated G-Hb was dialyzed against distilled water at 4° C. for four days.

Preparation of Glycated Bovine Serum Albumin (G-BSA)

A solution containing 0.3 g BSA (Sigma, fatty acid free), 0.72 g D(+)- glucose (Sigma) and 2 mg sodium azide (Fisher) in 10 ml PBS (0.1 mol/l, pH 7.4 containing 25 mmol/l NaCl) was incubated for four days at 37° C. It was then dialyzed against distilled water for two days at 4° C. The final G-BSA concentration was measured as fructosamine using a RoTag kit (Roche) on a Cobas-Bio analyzer (Roche).

EXAMPLE 1

Inhibition of NBT - Gylcated BSA (G-BSA) Reaction by Meta-Aminophenylboronic Acid (APBA)

A solution of G-BSA (50 ul, 4.g mmol/l) was added to each of a series of wells of an Imulon polystyrene microtiter plate (mtp) (Dynatech Laboratories, Chantilly, Va.). A solution of APBA (50 ul concentration range 0-20 g/l) in an ammonium acetate buffer (250 mmol/l, pH 9.3) containing magnesium chloride (50 mmol/l) and sodium azide (0.2 g/l) was added to duplicate wells and the contents of the wells mixed briefly by agitation of the mtp. A solution of NBT (100 ul, 0.25 mmol/l in 0.1 mol/l carbonate buffer, pH 10.35) and 30 ul sodium hydroxide (1 mol/l) was then added to each well, the contents of the wells mixed briefly by agitation, and the absorbance at 540 nm measured (Dynatech MR 700 spectrophotometer) after a ten minute incubation at 37° C. Duplicate wells containing 50 ul PBS, 100 ul NBT and 30 ul sodium hydroxide served as the assay blank. The experiment was repeated using 0.02–0.25 umoles G-BSA.

Figure 2:
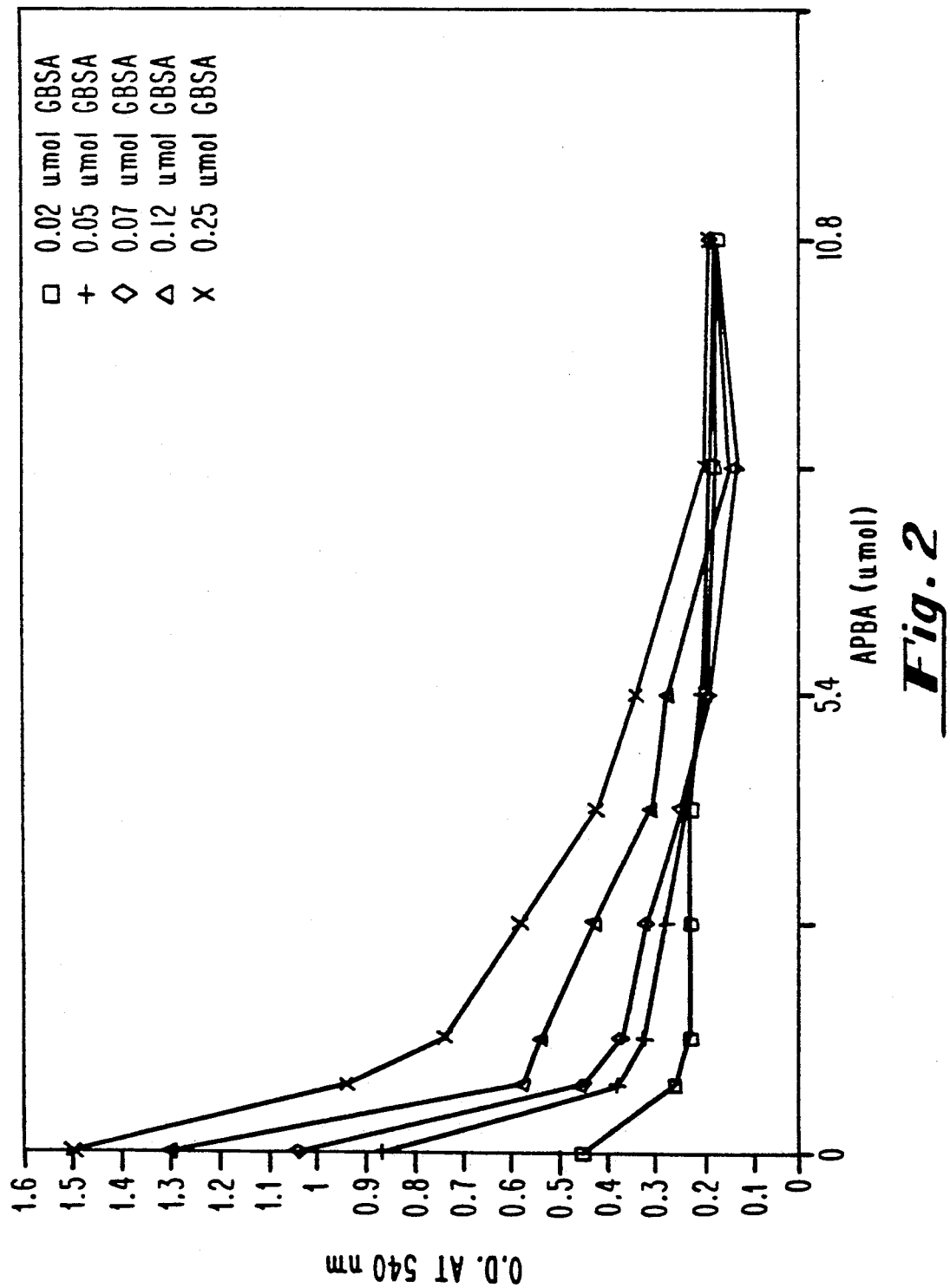
FIG. 2—Effect Of Varying meta-aminophenylboronic acid (APBA)(at different levels of Gly-Albumin).

As shown in FIG. 2, APBA inhibited the NBT-G-BSA reaction at all levels of G-BSA tested, and the inhibition was a function of the APBA concentration.

EXAMPLE 2

Inhibition of NBT - DMF Reaction by APBA

The experimental protocol described in EXAMPLE 1 was followed and G-BSA was replaced by different amounts of a DMF standard (3.2 mmol/l, Roche Diagnostics, Nutley, N.J.) to give 0.016–0.16 mmoles DMF/well.

Figure 3:
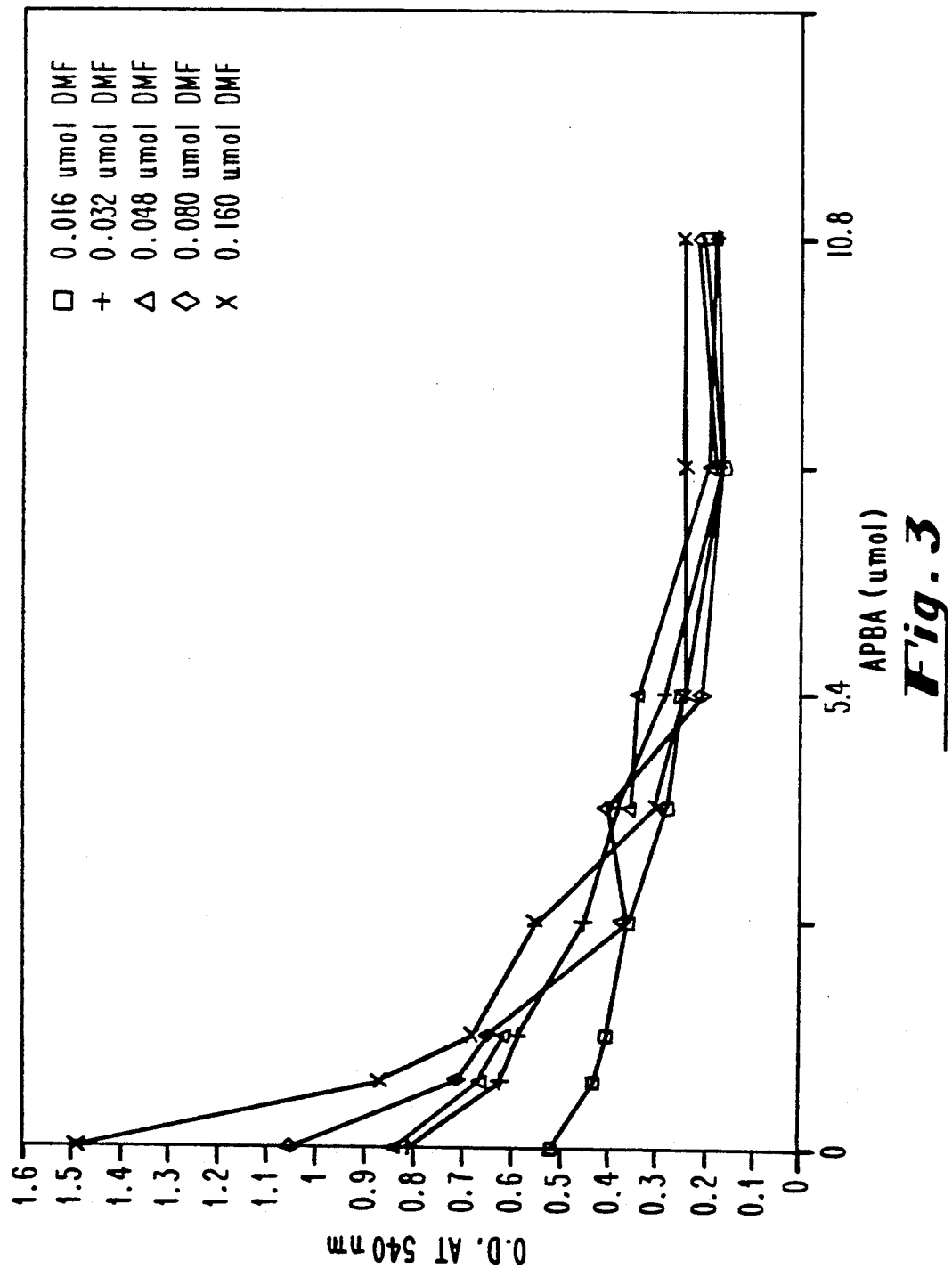
FIG. 3—Effect Of Varying meta-aminophenylboronic acid (using DMF).

Experimental results are shown in FIG. 3. APBA inhibited the reaction between NBT and this synthetic fructosamine (DMF).

EXAMPLE 3

Inhibition of NBT - Fructose Reaction by APBA

The experimental protocol described in EXAMPLE 1 was followed and G-BSA was replaced by 50 ul of dilutions of fructose (4 mmol/l, Sigma) in PBS (0.02–0.2 umoles/well).

Figure 4:
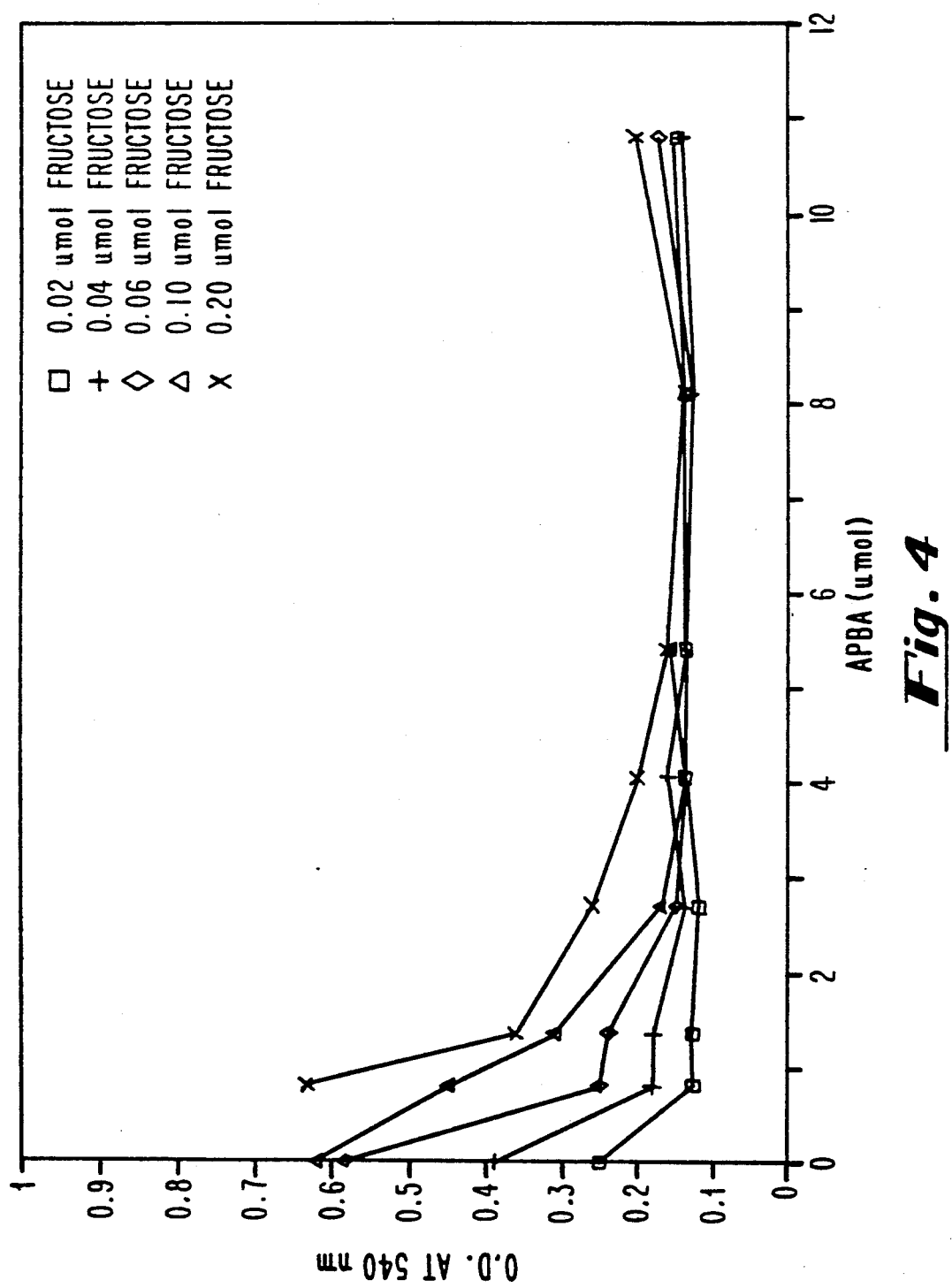
FIG. 4—Effect Of APBA On NBT-Fructose reaction (at different levels of Fructose).

Experimental results are shown in FIG. 4. APBA inhibited the reaction between NBT and fructose at all levels of fructose tested.

EXAMPLE 4

Inhibition of NBT - G-BSA (Absorbed) Reaction by APBA 50 ul of a solution of G-BSA (4.9 mmol/l) in PBS buffer was absorbed to the inside surface of a series of wells of polystyrene microtiter plate by evaporation overnight at RT, with agitation. The influence of APBA on the reaction of the absorbed G-BSA was studied using the protocol described in EXAMPLE 1.

Figure 5:
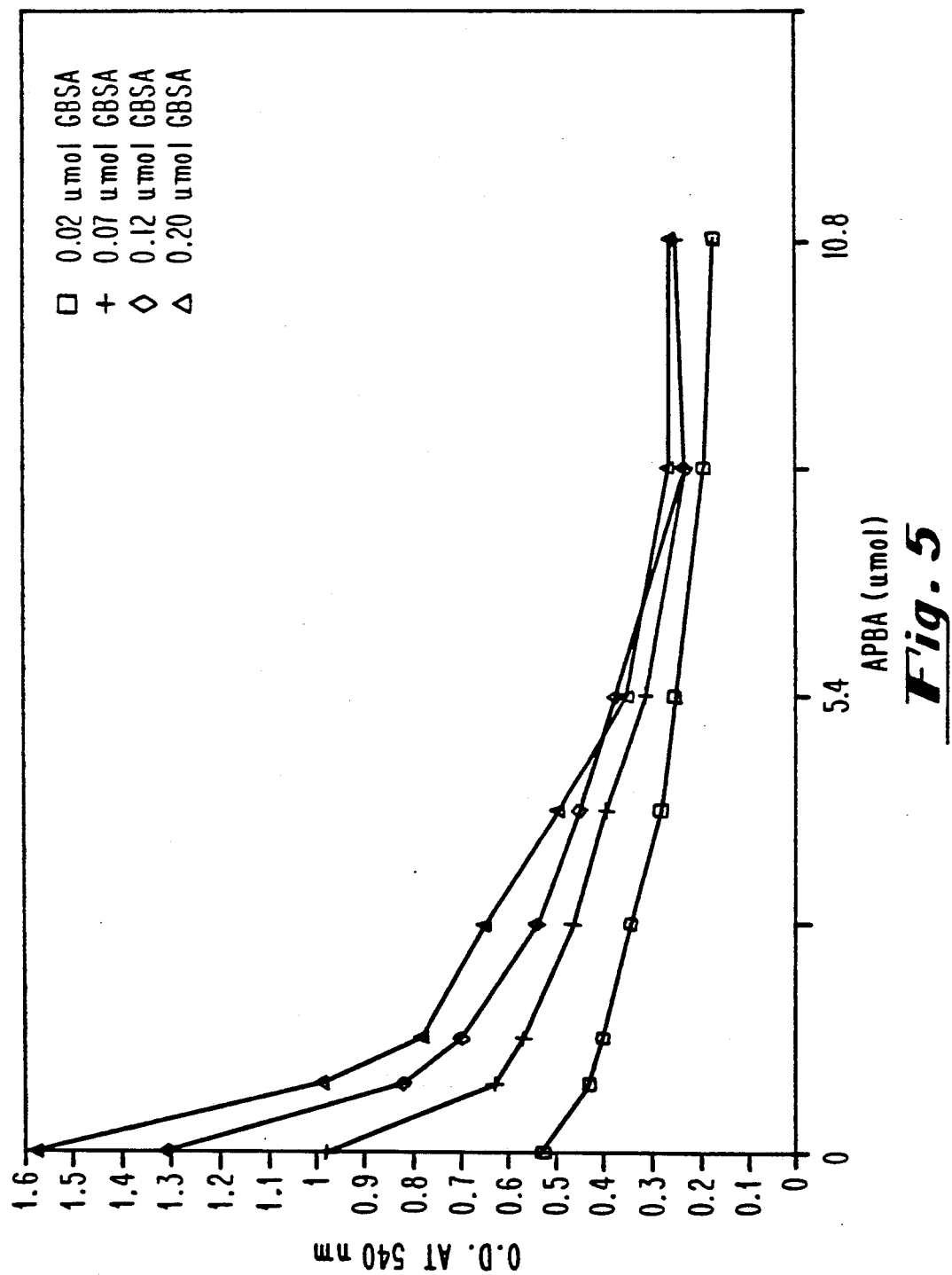
FIG. 5—Effect Of Varying meta-aminophenylboronic acid (using Albumin evaporated in wells of a microtiter plate).

Experimental results are shown in FIG. 5 where it can be seen that APBA inhibited the reaction between NBT and G-BSA in a concentration dependent manner. Maximal inhibition for a 0.2 μmol G-BSA solution was obtained with 8.1 μmol of APBA.

EXAMPLE 5

Kinetics of DMF: APBA Reaction

A solution of DMF standard (50 ul, 3.2 mmol/l) was added to each of a series of mtp wells. APBA (50 ul, 50 mmol/l) was added to duplicate wells at timed intervals (0, 2, 5, 10, 20 and 30 minutes). Free DMF was then measured using NBT as described in EXAMPLE 1. The experiment was repeated using different concentrations of APBA (0.025, 0.07 and 0.107 mol/l).

Figure 6:
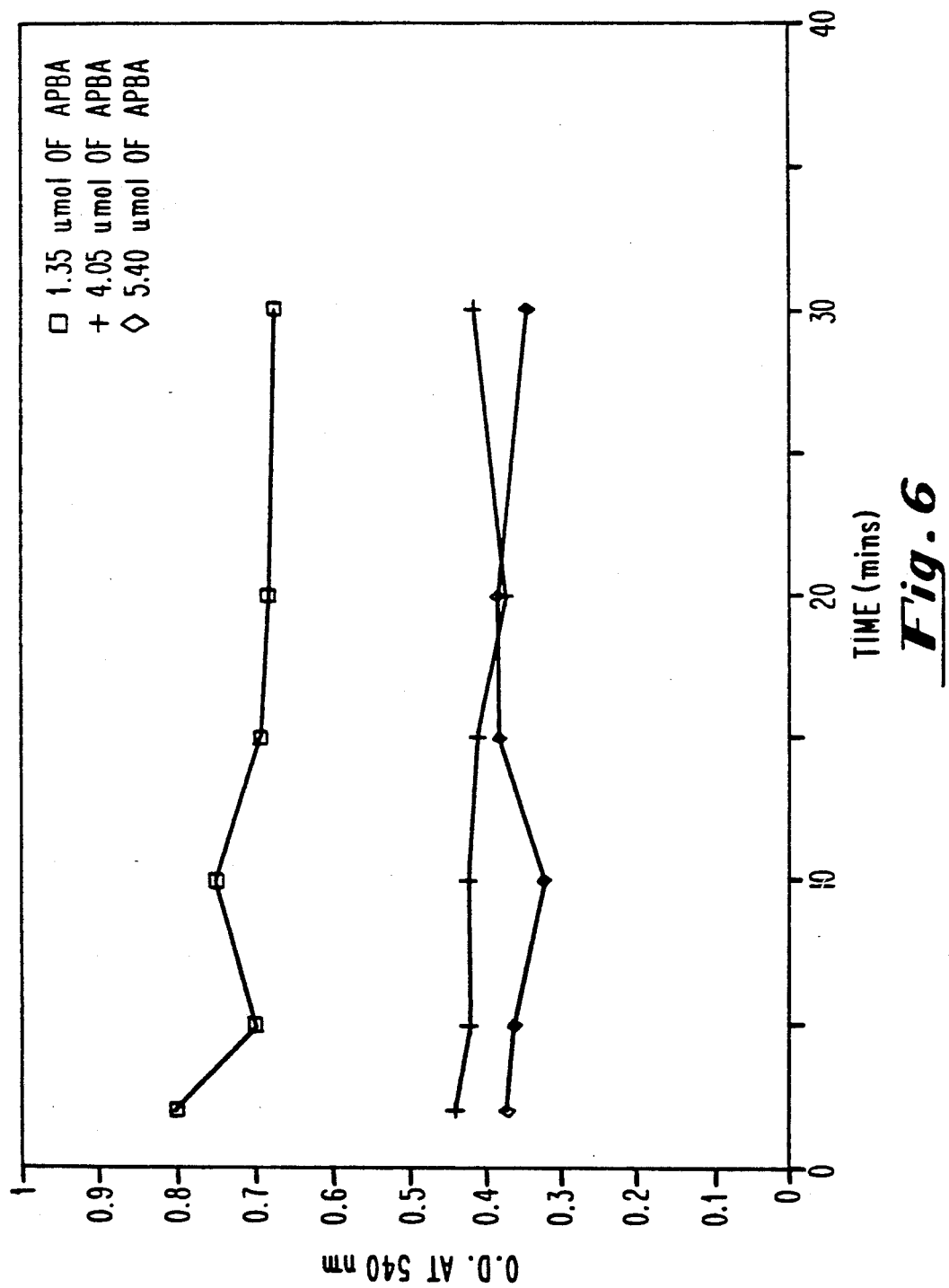
FIG. 6—Kinetics Of NBT-DMF-APBA Reaction.

Experimental results are shown in FIG. 6. The results show that the reaction is rapid and is complete within approximately two minutes.

EXAMPLE 6

Kinetics of G-BSA: APBA Reaction

The experimental protocol described in EXAMPLE 5 was followed and the DMF standard was replaced by 50 ul of G-BSA (4.9 mmol/l). The experiment was repeated with 25 ul of G-BSA.

Figure 7:
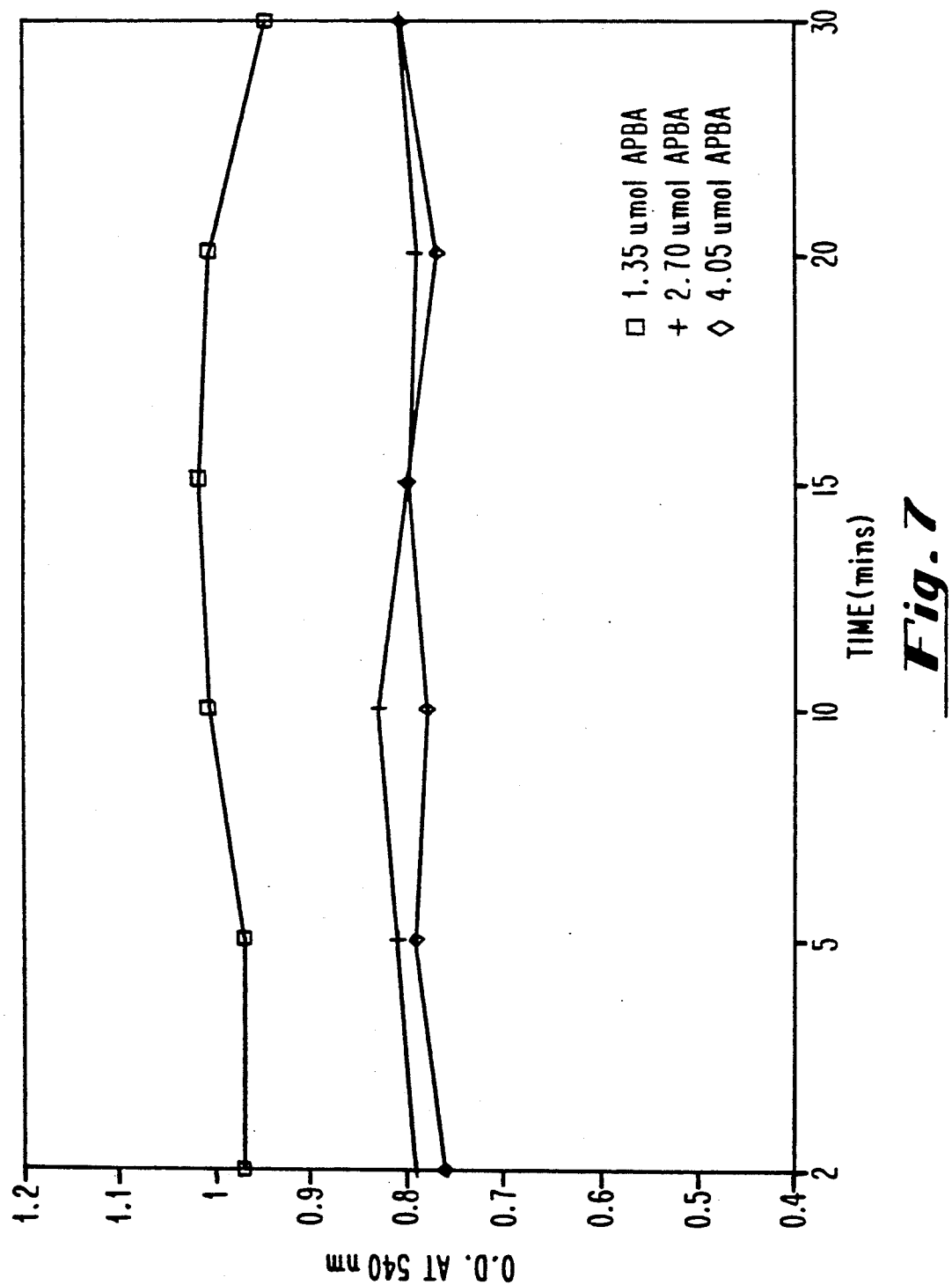
FIG. 7—Kinetics Of NBT-glycated albumin (Gly-ALB)APBA.

Experiment results are shown in FIG. 7. The results show that the reaction is rapid and is complete within approximately two minutes.

EXAMPLE 7

Inhibition of the NBT - G-BSA (Absorbed) Reaction by 4-Bromophenylboronic Acid (BBA)

The experimental protocol described in EXAMPLE 4 was followed and the APBA was replaced by BPBA (99 mmol/l in a pH 9.3 ammonium acetate-magnesium chloride buffer).

Figure 8:
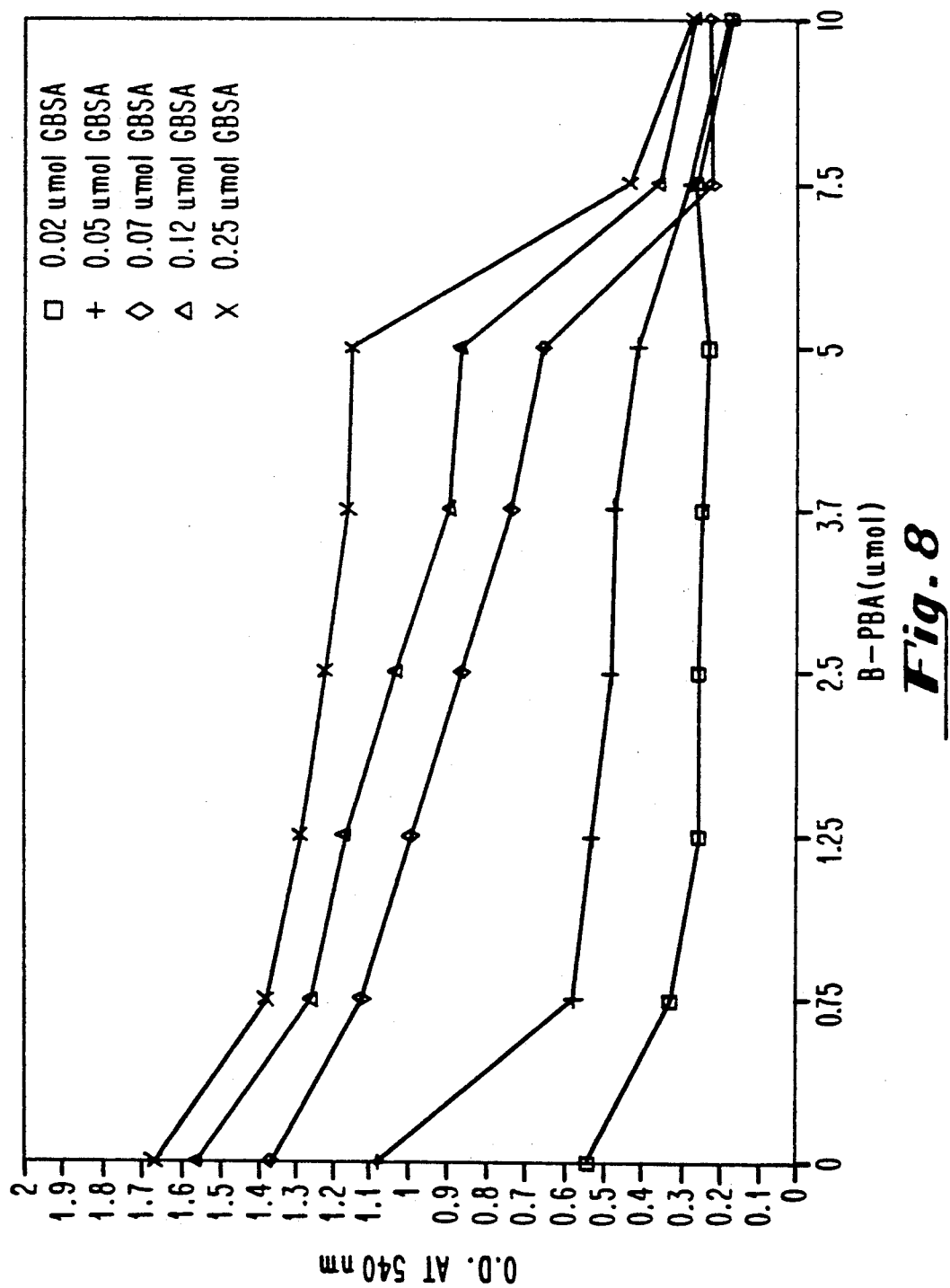
FIG. 8—Effect Of Bromophenylboronic acid On NBT/glycated bovine serum albumin (GBSA) Reaction.

Experimental results are shown in FIG. 8. BPBA inhibited the reaction in a dose dependent manner.

EXAMPLE 8

Inhibition of the NBT-G-BSA Reaction by Nitrophenylboronic Acid (NPBA)

Figure 9:
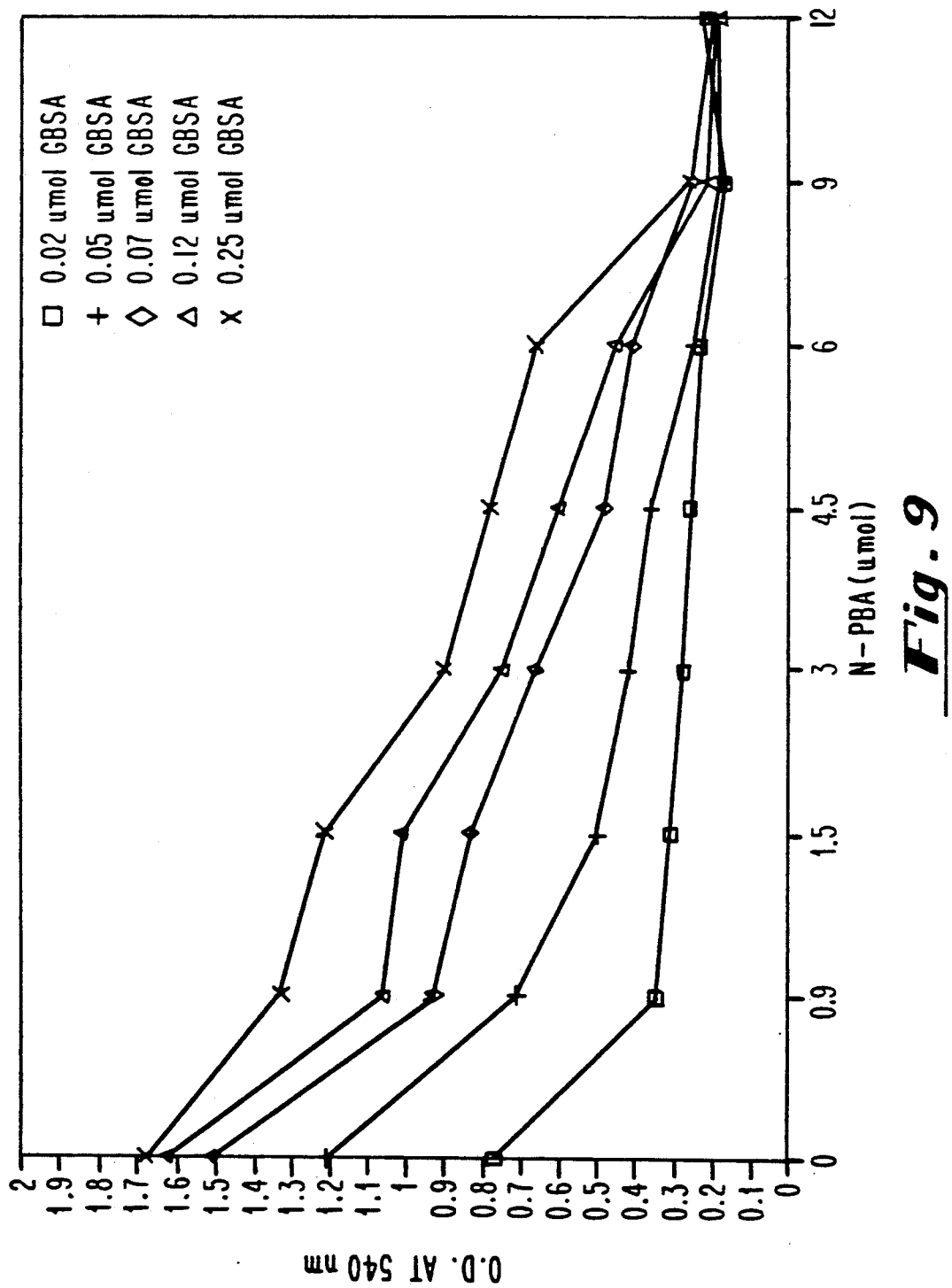
FIG. 9—Effect Of Nitrophenylboronic acid On NBT/GBSA Reaction.

The experimental protocol described in EXAMPLE 4 was followed and the APBA was replaced by BPBA (99 mmol/l in a pH 9.3 ammonium acetate-magnesion chloride buffer). Experimental results are shown in FIG. 9. The NPBA inhibited the NBT-G-BSA reaction at all concentrations of G-BSA tested.

EXAMPLE 9

Inhibition of the NBT - G-BSA Reaction by Phenylboronic Acid (PBA)

Figure 10:
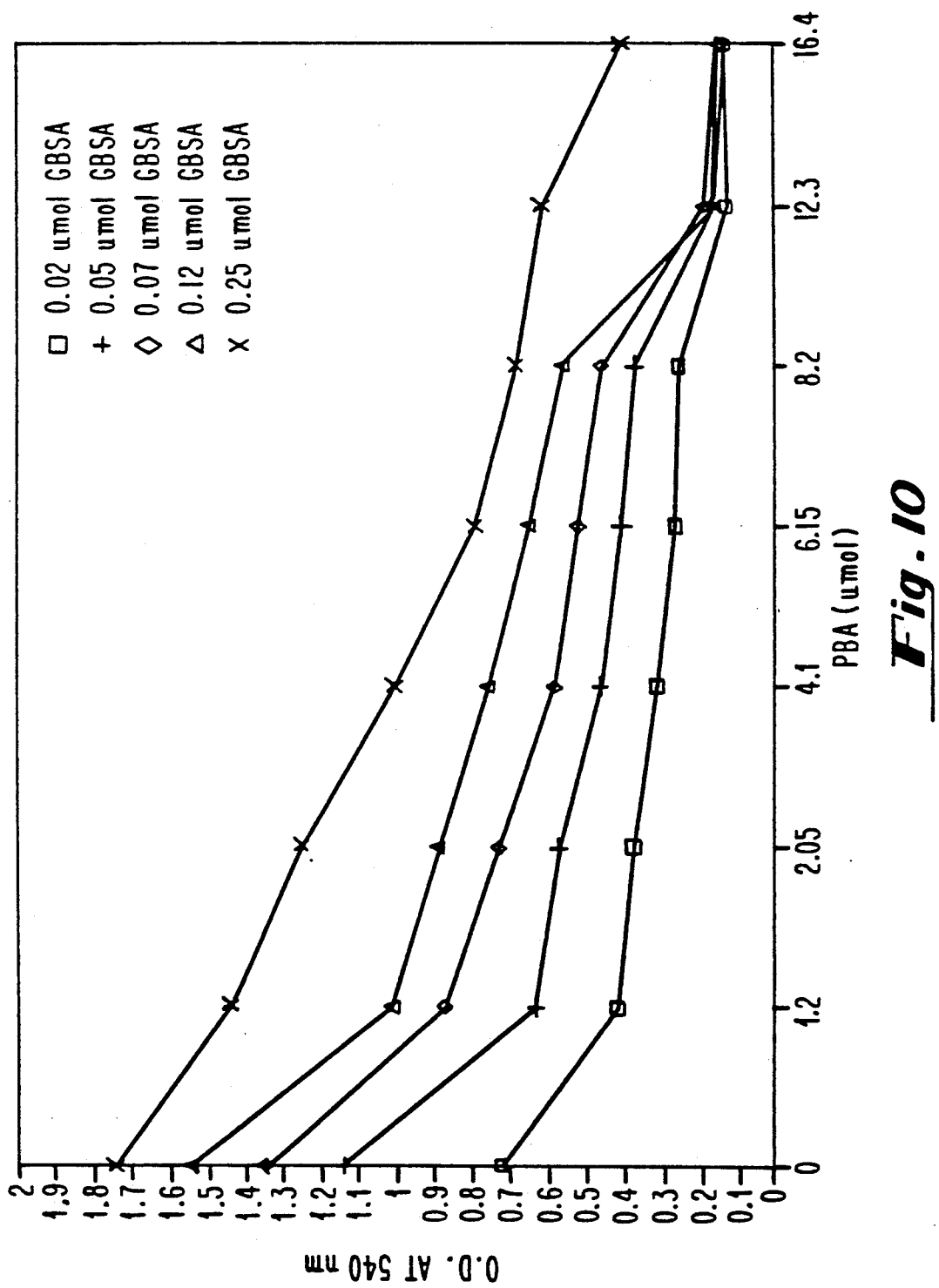
FIG. 10—Effect Of Phenylboronic acid On NBT/GBSA Reaction.

The experimental protocol described in EXAMPLE 1 was followed and the APBA replaced by PBA (0–125 mmol/l). Experimental results are shown in FIG. 10. The parent phenylboronic acid inhibited the NBT-G-BSA reaction at all concentrations of G-BSA tested.

EXAMPLE 10

Competition Between G-BSA (Absorbed) and Sorbitol for APBA

G-BSA (50 ul, 4.9 mmol/l) was absorbed onto the inside surface of polystyrene mtp wells as described in EXAMPLE 4. Sorbitol (50 ul, 0–60 mmol/l in PBS) was added to a series of duplicate wells and the contents of the wells incubated for fifteen minutes at room temperature. APBA (50 ul, 54 mmol/l) was added to each well, the contents of the wells mixed briefly by agitation, and then incubated for ten minutes at room temperature. G-BSA was then assayed using NBT as described in EXAMPLE 1 (sorbitol does not react with NBT). The experiment was repeated different concentrations of G-BSA.

Figure 11:
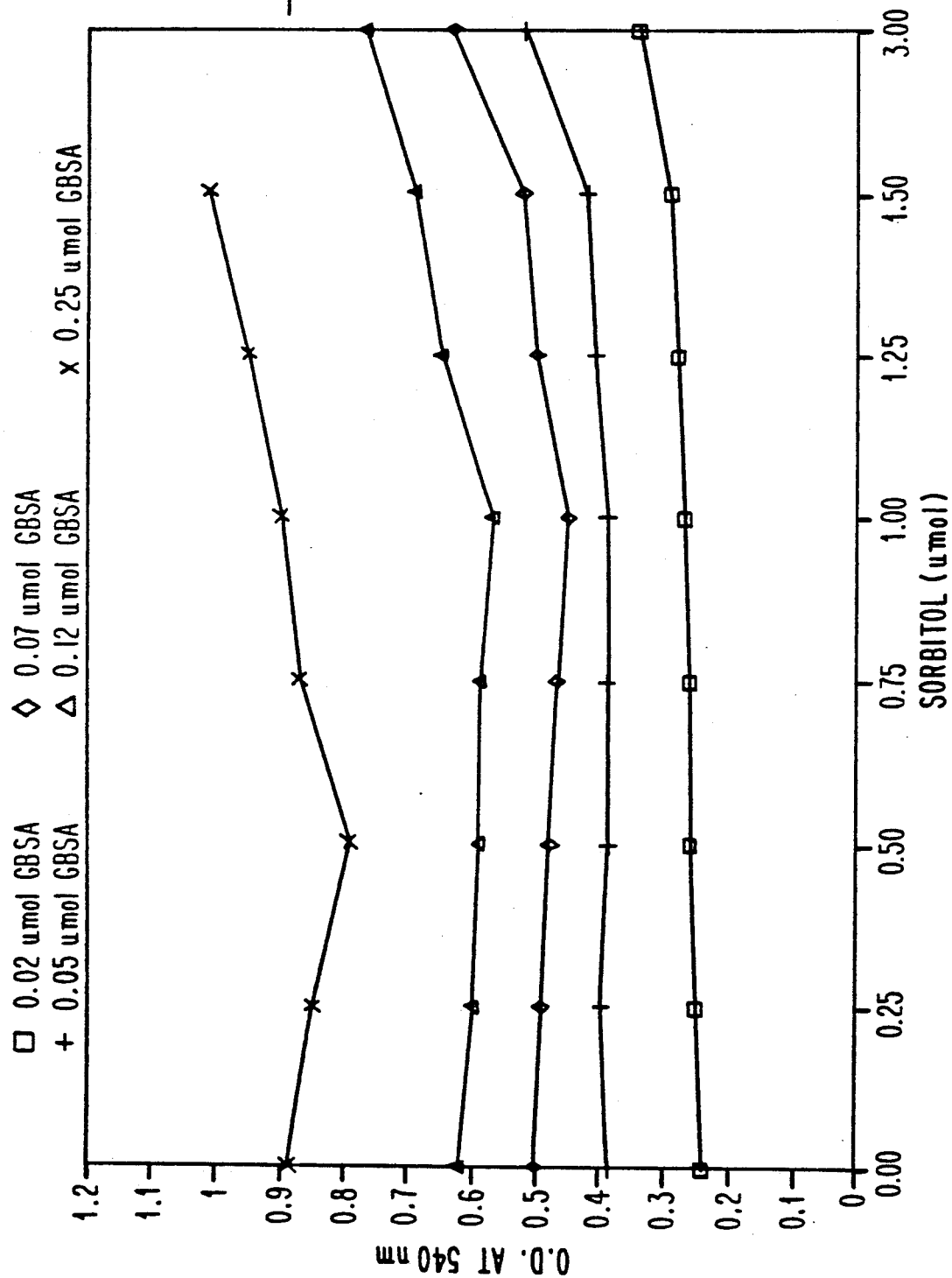
FIG. 11—Effect Of Sorbitol On NBT/GBSA (GBSA absorbed, APBA cte).

Experimental results are shown in FIG. 11. Sorbitol reduced the inhibition by APBA of the NBT-G-BSA reaction be competing with G-BSA for binding sites on APBA. This was most pronounced as the amount of sorbitol was increased.

EXAMPLE 11

Competition Between G-BSA and Glycated Hemoglobin (G-Hb) for APBA

A solution of G-BSA (50 ul, 7.2 mmol/l) was added to the wells of a mtp. G-Hb (100 ul, 2 mmol/l) was added to each well and the contents of the well mixed. APBA (50 ul) in the concentration range 0–0.27 mmol/l, was added to a series of duplicate wells, and the contents of the wells incubated for ten minutes at room temperature. G-BSA in the wells was measured using NBT as described in EXAMPLE 1. Wells in which the G-Hb was replaced by 100 ul PBS served as controls. The experiment was repeated using 15 ul of the G-BSA solutions.

Figure 12:
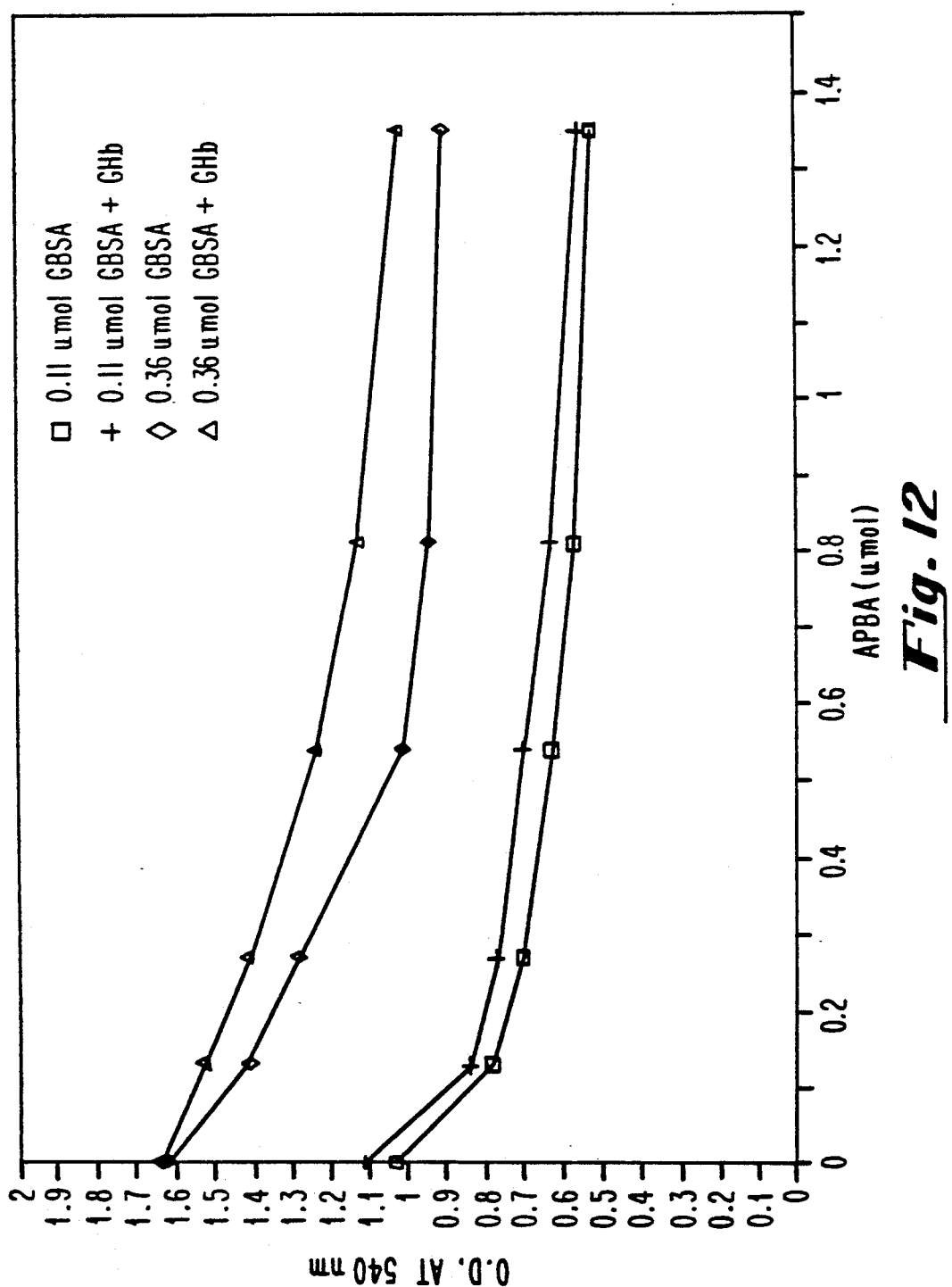
FIG. 12—Effect Of glycated hemoglobin (GHb) On NBT/GBSA/APBA Reaction.

Experimental results are shown in FIG. 12. Less inhibition occurred in the presence of G-Hb due to the competition between G-Hb and G-BSA for APBA.

EXAMPLE 12

Competition Between G-BSA and Sorbitol for APBA

A solution of G-BSA (50 ul, 7.2 mmol/l) and 50 ul of an aqueous sorbitol solution (0–60 mmol/l) were added to a series of duplicate mtp wells. APBA (50 ul, 54 mmol/l) was added to each well and the contents of the well incubated for fifteen minutes with occasional agitation at room temperature. G-BSA in wells was measured using NBT as described in EXAMPLE 1. The experiment was repeated using 5, 10, 15 and 25 ul of the G-BSA.

Figure 13:
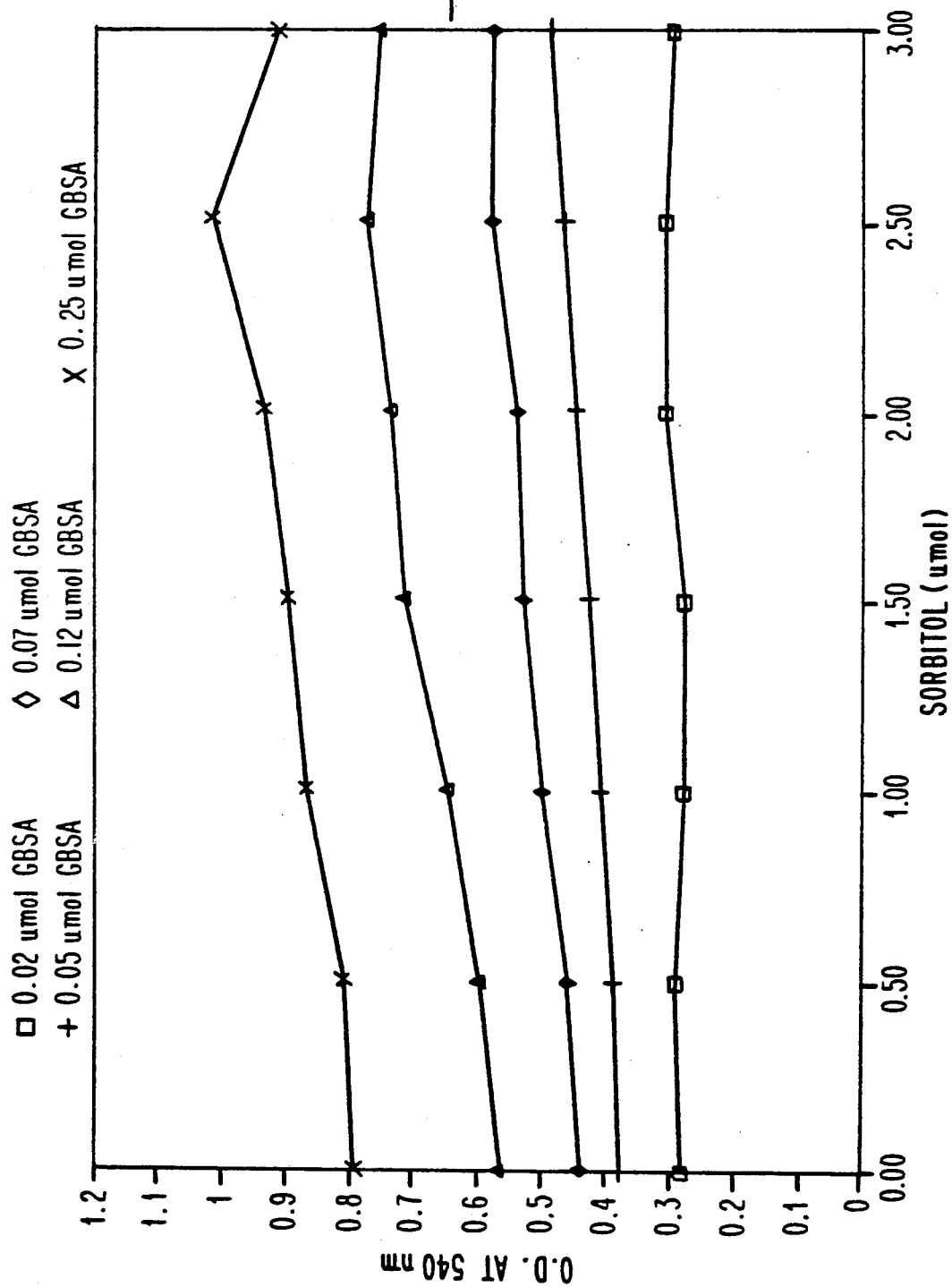
FIG. 13—Effect Of Sorbitol On NBT/GBSA/APBA (GBSA in solution—APBA cte:2.7 umol).

Experimental results are shown in FIG. 13. Sorbitol reduced the inhibition by APBA of the NBT G-BSA reaction in a concentration dependent manner.

EXAMPLE 13

Inhibition of MTT - G-BSA Reaction by APBA

The experimental protocol described in EXAMPLE 1 was followed except that NBT was replaced by 3-(4,5-dimethylthiazol-2-yl)-2, 5-phenyltetrazolium bromide (MTT) 0.25 mmol/l (Sigma).

Figure 14:
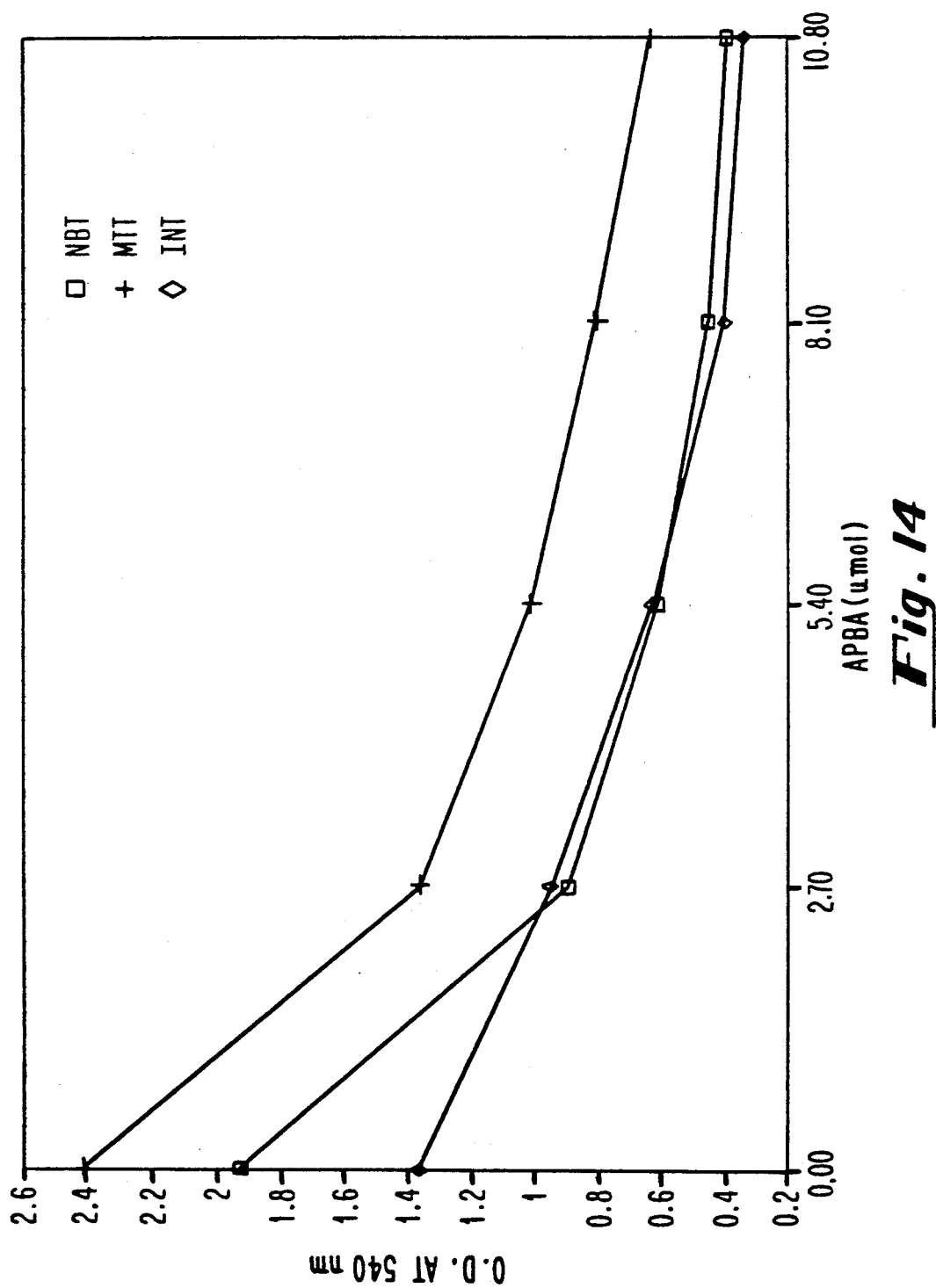
FIG. 14—Different tetrazolium (TZ) salts (with GBSA cte: 0.25 umol).
Figure 15:
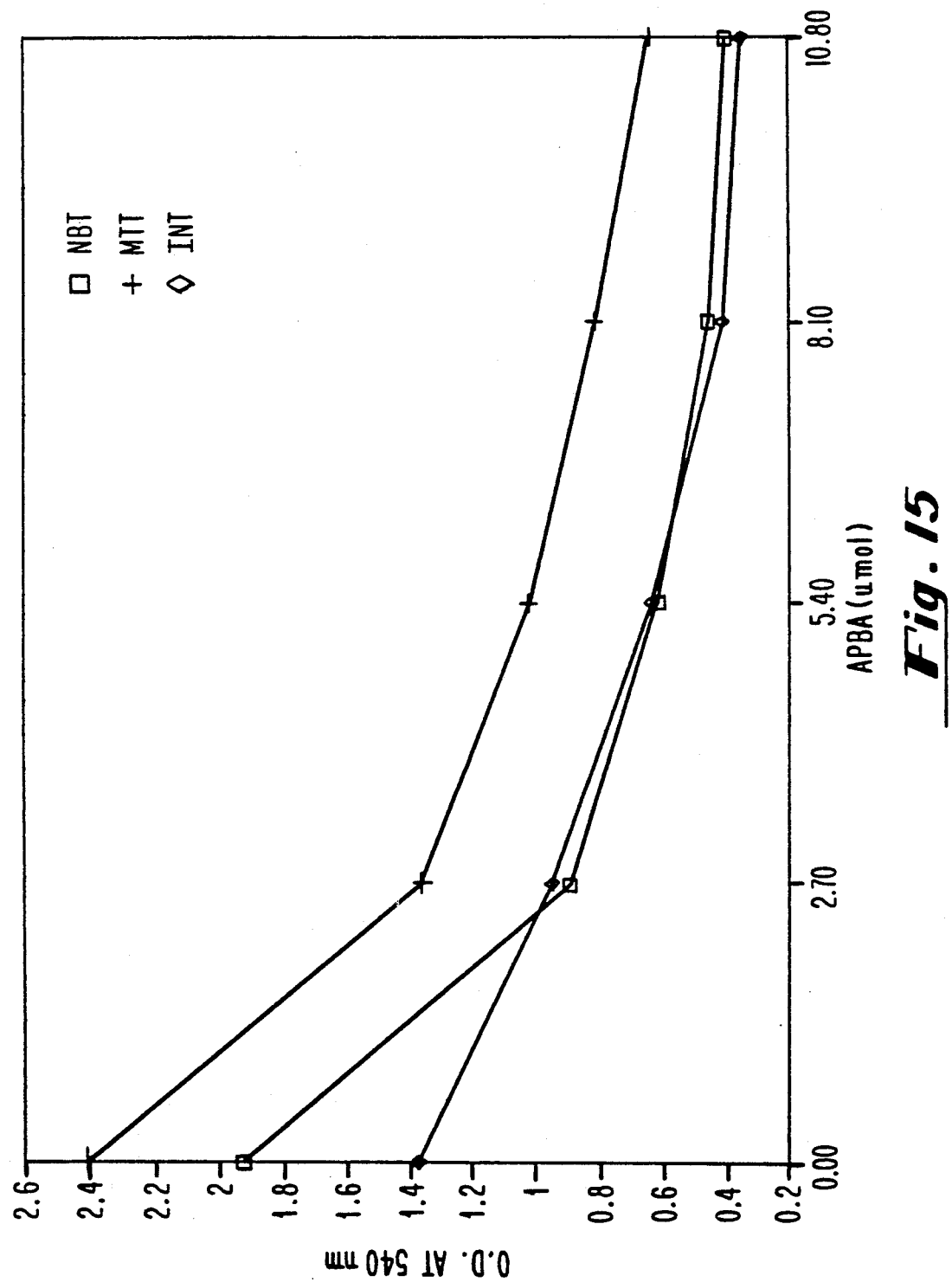
FIG. 15—Different TZ salts (with GBSA cte: 0.25 umol).

The experimental results are shown in FIG. 14, and indicate that MTT is an effective replacement for NBT as an indicator in this assay.

EXAMPLE 14

Inhibition of INT - G-BSA Reaction by APBA

The experimental protocol described in EXAMPLE 1 was followed except that NBT was replaced by p-iodonitrotetrazolium violet (INT) 0.25 mmol/l (Sigma).

The experimental results are shown FIG. 14. INT is an alternative indicator to NBT but under these conditions it is not as sensitive.

EXAMPLE 15

Preparation of Glycoslyated HSA Immobilized on a Memtek Membrane

A 2×2 mm piece of membrane (Memtek, Billerica, Mass.) was washed in a carbonate buffer (0.5 mol/l, pH 9.3) and then incubated with 15 ml HSA (0.045 umol/ml, Sigma) in PBS (pH 7.4) for one hour at room temperature. The membrane was washed with PBS containing 1% Tween 20 (PBS-Tween) and then incubated with 10 ml of D(+) glucose (8 umol/ml) in PBS (pH 7.4) for five days at 37° C. The membrane was then washed with PBS-Tween and stored dry at 40° C.

EXAMPLE 16

Preparation of Glycosylated HSA Immobilized on a Pall Biodyne Membrane

A 2×2 cm piece of Biodyne membrane (Pall, Glen Cover, N.Y.) was incubated with HSA, washed and stored as described in EXAMPLE 15.

EXAMPLE 17

Qualitative Assay of G-HSA Immobilized on Membranes

A solution of NBT containing sodium hydroxide (130 ul, see EXAMPLE 1) was pipetted onto the membrane and the membrane incubated at 37° C. for ten minutes.

The various native membranes tested gave variable blank reactions with NBT and in the best examples the native Pall Biodyne membrane was negative and the Memtek very weakly positive with NBT. In contrast both types of immobilized G-HSA membrane gave a strongly positive NBT reaction (intense purple coloration).

EXAMPLE 18

Inhibition of the NBT - Membrane Immobilized G-HSA Reaction by APBA

APBA (100 ul, 0–0.54 mol/l) was pipetted onto a 1×1 cn piece of immobilized G-HSA membrane and the membrane incubated at room temperature for one hour. G-HSA on the membrane was then assayed using NBT as described in EXAMPLE 17.

Various degrees of inhibition of the NBT reaction were obtained and in the best example (Memtek) the immobilized G-HSA membrane gave a positive NBT reaction (intense purple coloration) and the APBA (100 ul) treated membrane gave a weakly positive reaction. Lesser amounts of APBA gave a graded response in the NBT reaction.

EXAMPLE 19

Competition Between Glycated Proteins in Whole Blood and Membrane Immobilized G-HSA for APBA A whole blood specimen from a patient with poor glucose control, glycoslylated hemoglobin (G-Hb) 20% (reference interval, 5–8.5%) was used to test the membranes.

Three pieces of immobilized G-HSA Memtek membrane were treated as follows:

1. CONTROL

Membrane reacted with NBT as described in EXAMPLE 17.

2. BLANK

The whole blood (50 ul) was lysed by mixing with 400 ul of Glyc-Affin lysing reagent (Isolab). The lysate (100 ul) was added to the membrane and incubated for several hours. The membrane was then reacted with NBT as described in EXAMPLE 17.

3. TEST

Lysed blood (100 ul) was mixed with APBA (100 ul, 108 mmol/l) and the mixture pipetted onto membrane and the membrane incubated for several hours. It was then reacted with NBT as described in EXAMPLE 17.

Visual inspection of the membranes revealed that the Control gave a strongly positive reaction, the Blank gave positive reaction and the Test gave a negative reaction consistent with inhibition of the immobilized G-HSA by APBA not complexed to the G-Hb.

EXAMPLE 20

Inhibition of NBT - G-BSA Reaction by Boric Acid

The experimental protocol described in EXAMPLE 1 was followed and the APBA replaced by boric acid (220 mmol/l).

Figure 16:
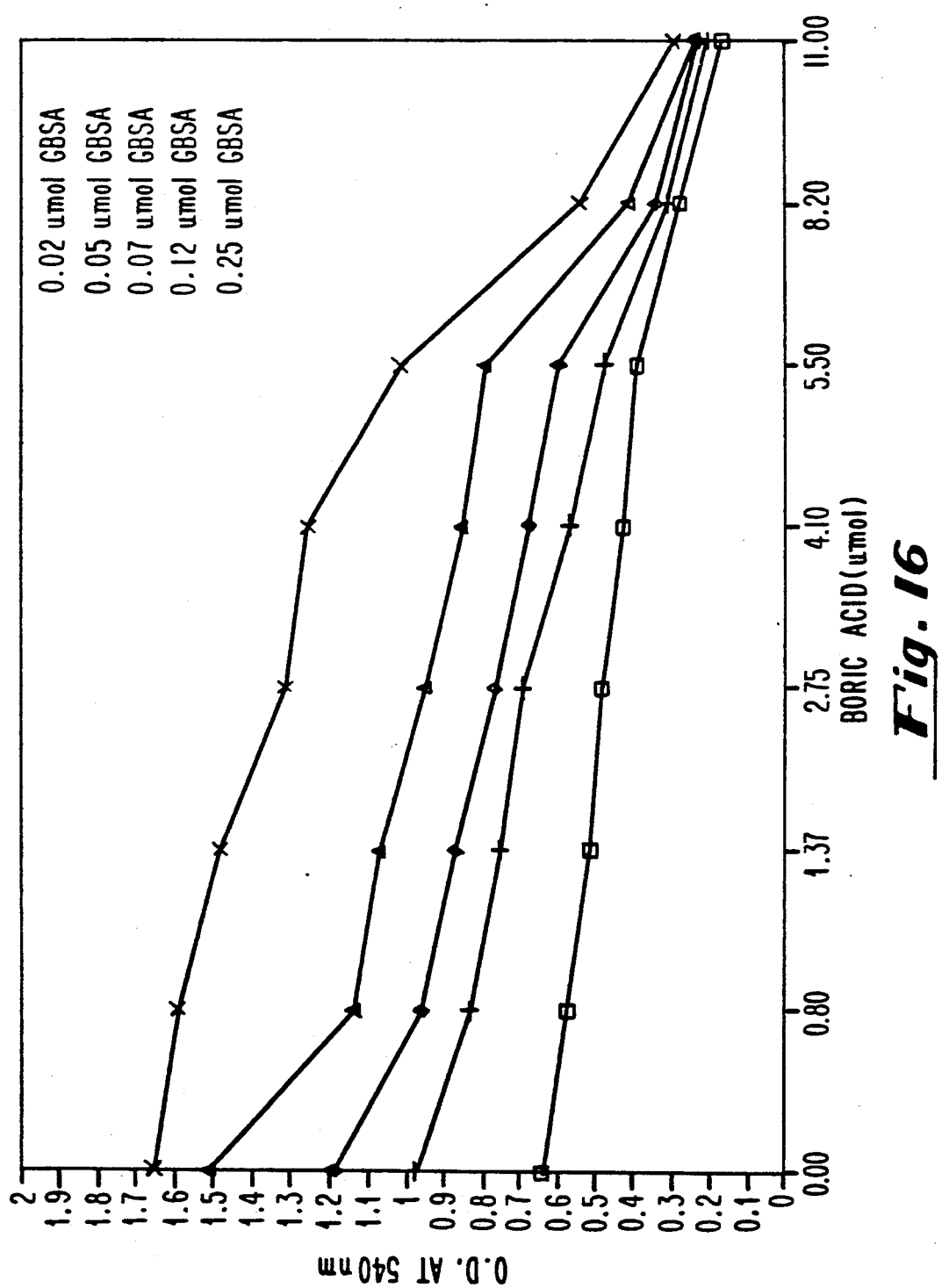
FIG. 16—Effect Of Boric Acid On NBT/GBSA reaction.

Experimental results are shown in FIG. 16. Boric acid inhibited the NBT-G-BSA reaction in a concentration dependent manner. The shape of the dose response curve differed from those obtained with the phenylboronic acids. A more linear relationship was observed between the inhibition and boric acid concentration.

We claim:

1. A method of detecting glycated protein in a body fluid suspected of containing said glycated protein, comprising the steps of:
   a) contacting a test sample of said body fluid with an excess of a binder composition under conditions which allow binding of glycated protein in said test sample to a portion of said binder composition thereby leaving a portion of said binder composition unbound with glycated protein;
   b) exposing the unbound portion of said binder composition from step a to an excess of glycated compound affixed to a solid support under conditions which allow reaction of said unbound portion of said binder composition to a portion of said glycated compound affixed to a solid support thereby leaving a portion of said glycated compound affixed to a solid support unreacted with said unbound portion of said binder composition;
   c) reacting the unreacted portion of said glycated compound affixed to a solid support from step b with a detecting agent; and
   d) detecting said detecting agent.

2. The method of claim 1 wherein the binding of step (a), the reaction of step (b), and the reaction step of (c) are each substantially quantitative.

3. The method of claim 1 wherein said glycated protein is glycated-albumin.

4. The method of claim 1 wherein said glycated protein is glycated-hemoglobin.

5. The method of claim 1 wherein said body fluid is whole blood.

6. The method of claim 1 wherein said body fluid is plasma.

7. The method of claim 1 wherein said binder composition is

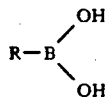

wherein R is hydroxyl, phenyl or substituted phenyl.

8. The method of claim 7 wherein said binder composition is meta-aminophenyl boronic acid.

9. The method of claim 7 wherein said binder composition is boric acid.

10. The method of claim 1 wherein said glycated compound affixed to a solid support is a glycated protein.

11. The method of claim 10 wherein said glycated protein affixed to a solid support is glycated albumin.

12. The method of claim 10 wherein said glycated protein affixed to a solid support is glycated polylysine.

13. The method of claim 1 wherein said detecting agent is a tetrazolium derivative or salt.

14. The method of claim 13 wherein said detecting agent is nitro blue tetrazolium.

15. The method of claim 13 wherein said detecting agent is 3-(4,5-dimethylthiazol-2-yl)-2,5-phenyltetrazolium bromide.

16. The method of claim 13 wherein said detecting agent is 5-phenyltetrazolium bromide.

17. The method of claim 1 wherein said detecting step is performed by visual inspection of said detecting agent.

18. The method of claim 1 wherein said body fluid is serum.

19. A method of detecting chronic hyperglycemia in mammals, comprising
   a) contacting a test sample of a body fluid from a mammal suspected of containing glycated protein with an excess of a binder composition under conditions which allow binding of glycated protein in said test sample to a portion of said binder composition thereby leaving a portion of said binder composition unbound with glycated protein;
   b) exposing the unbound portion of said binder composition from step a to an excess of glycated compound affixed to a solid support under conditions which allow reaction of said unbound portion of said binder composition to a portion of said glycated compound affixed to a solid support thereby leaving a portion of said glycated compound affixed to a solid support unreacted with said unbound portion of said binder composition;
   c) reacting the unreacted portion of said glycated compound affixed to a solid support from step b with a detecting agent; and
   d) detecting said detecting agent
   whereby the presence of detecting agent indicates the presence of glycated protein in said test sample and the presence in said mammal of chronic hyperglycemia.

20. The method of claim 19 wherein said mammal is a human.

21. The method of claim 19 wherein said body fluid is whole blood.

22. The method of claim 19 wherein said body fluid is plasma.

23. The method of claim 19 wherein said body fluid is serum.

24. The method of claim 19 wherein said binder composition is

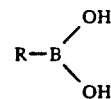

wherein R is hydroxyl, phenyl or substituted phenyl.

25. The method of claim 24 wherein said binder composition is meta-aminophenyl boronic acid.

26. The method of claim 24 wherein said binder composition is boric acid.

27. The method of claim 19 wherein said glycated compound affixed to a solid support is a glycated protein.

28. The method of claim 27 wherein said glycated protein affixed to a solid support is glycated albumin.

29. The method of claim 27 wherein said glycated protein affixed to a solid support is glycated polylysine.

30. The method of claim 19 wherein said detecting agent is a tetrazolium derivative or salt.

31. The method of claim 30 wherein said detecting agent is nitro blue tetrazolium.

32. The method of claim 30 wherein said detecting agent is 3-(4,5-dimethylthiazol-2-yl)-2,5-phenyltetrazolium bromide.

33. The method of claim 30 wherein said detecting agent is 5-phenyltetrazolium bromide.

* * * * *